(12) United States Patent
Podoleanu

(10) Patent No.: US 7,841,719 B2
(45) Date of Patent: Nov. 30, 2010

(54) METHOD AND APPARATUS FOR DETERMINING THE SHAPE, DISTANCE AND ORIENTATION OF AN OBJECT

(75) Inventor: Adrian G. H. Podoleanu, Canterbury (GB)

(73) Assignee: OTI Ophthalmic Technologies Inc (CA)

(*) Notice: Subject to any disclaimer, the term of this patent is extended or adjusted under 35 U.S.C. 154(b) by 356 days.

(21) Appl. No.: 12/019,121

(22) Filed: Jan. 24, 2008

(65) Prior Publication Data
US 2008/0170204 A1    Jul. 17, 2008

Related U.S. Application Data

(63) Continuation-in-part of application No. PCT/CA2007/000212, filed on Feb. 14, 2007.

(30) Foreign Application Priority Data

Feb. 15, 2006  (GB) ................. 0603035.7

(51) Int. Cl.
*A61B 3/10* (2006.01)
(52) U.S. Cl. .................. 351/212; 351/246; 356/479
(58) Field of Classification Search ............. 351/206, 351/207, 211, 212, 221, 246, 247; 356/479, 356/354, 345, 351, 349; 600/476
See application file for complete search history.

(56) References Cited

U.S. PATENT DOCUMENTS 5,975,697 A    11/1999  Podoleanu et al.
6,111,645 A    8/2000   Tearney et al.
7,330,273 B2 * 2/2008   Podoleanu et al. .......... 356/497
7,505,142 B2 * 3/2009   Knighton et al. ............ 356/479
2003/0199769 A1  10/2003  Podoleanu et al.

FOREIGN PATENT DOCUMENTS

| CA | 2519937 A1 | 10/2004 |
|---|---|---|
| WO | WO 01/01849 A1 | 1/2001 |
| WO | WO 2006/023614 A2 | 3/2006 |

\* cited by examiner

*Primary Examiner*—Hung X Dang
(74) *Attorney, Agent, or Firm*—Lawrence E. Laubscher, Jr.

(57) ABSTRACT

A method of determining the external three dimensional external contour of a curved object in one step, which produces and processes a single composite en-face OCT image (a C-scan), which involves generating and processing a set of two dimensional image contours of the object in different image planes using a plurality of optical path lengths in an OCT system with all such contours present in the composite en-face OCT image. The multiple path lengths are generated using a multiple delay element in bulk or in fiber inserted in the path from the source to the OCT system or in one of the OCT arms. The image planes have a known spatial relationship with each other. The three dimensional external contour of the curved object is computed from the two dimensional contours in the composite en-face OCT image and the known spatial relationship between the image planes. Axial position and tilt of a sample are evaluated using an optimum shape object attached to the sample in one step, by processing a s composite en-face OCT image generated by using a plurality of optical path delays.

26 Claims, 7 Drawing Sheets

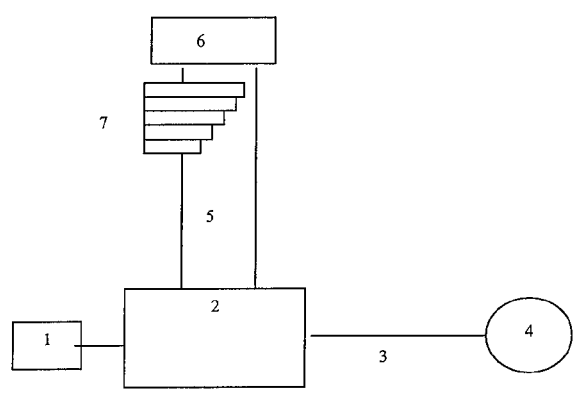
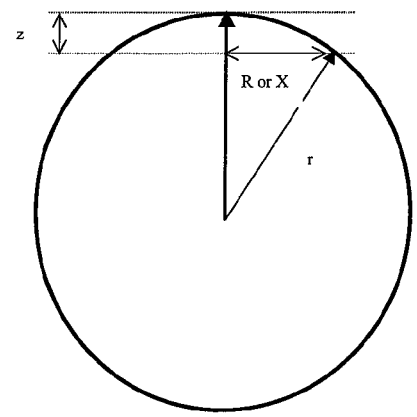
Fig. 4a Fig. 4b
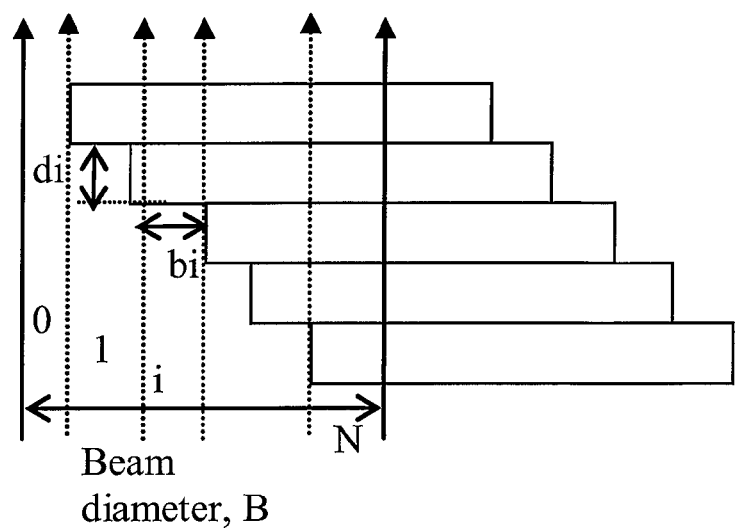
Fig. 5

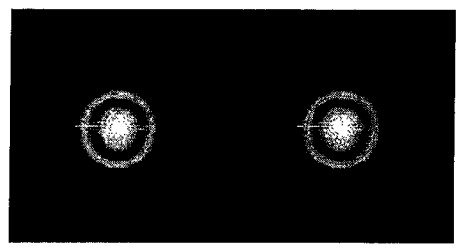
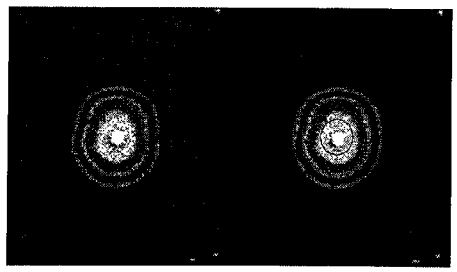
40 μm
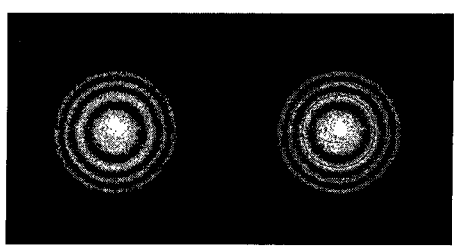
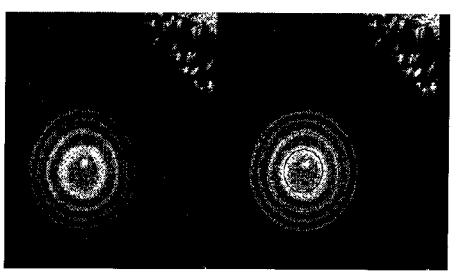
120 μm
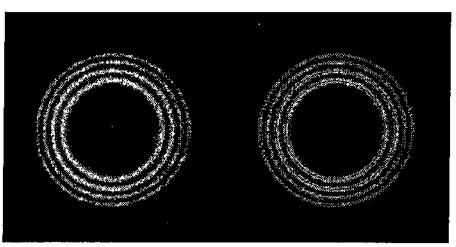
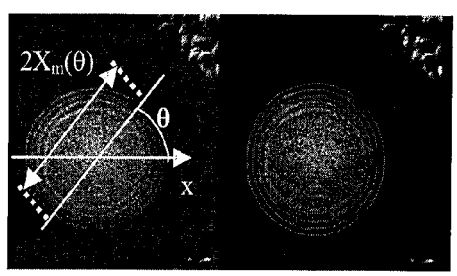
Fig. 8
Fig. 9
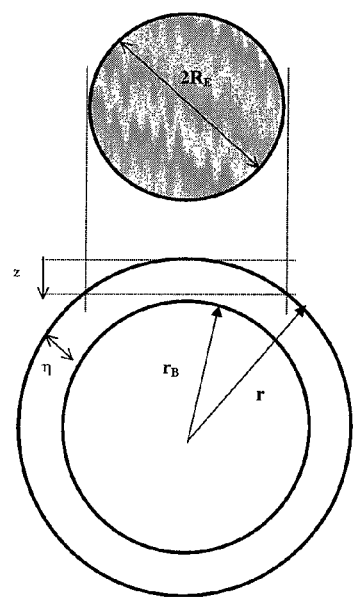
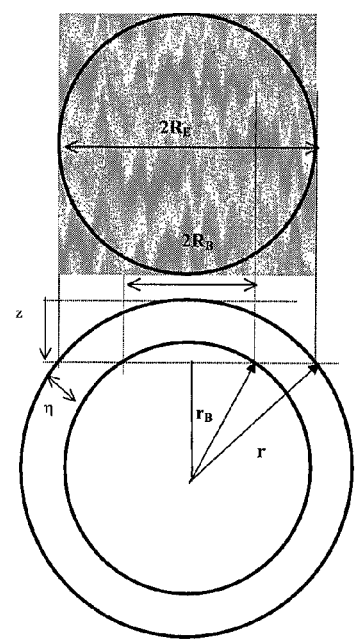
Fig. 10

METHOD AND APPARATUS FOR DETERMINING THE SHAPE, DISTANCE AND ORIENTATION OF AN OBJECT

CROSS REFERENCE TO RELATED APPLICATION

This application is a continuation-in-part of PCT application no. PCT/CA2007/00212, filed Feb. 14, 2007.

FIELD OF THE INVENTION

This invention relates to a method and apparatus for the measurement of curved objects, and in particular, for the topography of the cornea of the eye, and for evaluating the shape or axial position, of such objects, as well as for evaluation of the axial position and orientation of a plane.

BACKGROUND OF THE INVENTION

In the description which follows, reference is made primarily to the cornea of an eye, typically a human eye; however the invention is also applicable to measurements of lenses or any other curved objects which reflect visible or infrared light.

Optical coherence tomography (OCT) is a known technique for obtaining image information from within the eye using interferometric techniques. Longitudinal OCT has already been applied to measure the curvature and thickness of the cornea. Longitudinal OCT generates a B-scan image, which is a cross section image in the plane of lateral (angular direction) and depth in the tissue or axial distance from the instrument head. To proceed, a different ophthalmic instrument or a normal CCD camera is employed to acquire an en-face image of the cornea. A number of guiding radial lines are placed in this image over the cornea. OCT longitudinal cuts are subsequently acquired where the radial lines are placed, i.e. each longitudinal OCT contains one of such radial lines. Then the profiles of the epithelium and endothelium of the cornea in the B-scan images are used to determine the thickness and the curvature of the cornea. However, collecting a number of B-scans require time and the eye movements distort the profiles of the cornea collected.

The curvature of the cornea can also be inferred by using A-scans, which consist of line scans in the longitudinal direction, starting from a reference position and collecting A-scans of length just enough to acquire the peak corresponding to the cornea epithelium only. In this case only the curvature of the cornea is estimated. Again, as many A-scans are required, during the acquisition time, the axial eye movements lead to different axial positions of the cornea and so, to errors in the final profile.

OCT has also been reported as being capable of providing en-face images, as reported in "Coherence Imaging by Use of a Newton Rings Sampling Function" by A. Gh. Podoleanu, G. M. Dobre, D. J. Webb, D. A. Jackson, published in Opt. Lett., Vol. 21, No. 21, (1996), pp. 1789-1791, "Simultaneous En-face Imaging of Two Layers in Human Retina" Opt. Letters, by A. Gh. Podoleanu, G. M. Dobre, D. J. Webb, D. A. Jackson, published in Opt. Lett., 1997, vol. 22, No. 13, pp 1039-1041 and "En-face Coherence Imaging Using Galvanometer Scanner Modulation" by A. Gh. Podoleanu, G. M. Dobre, D. A. Jackson, Opt. Lett. 23, pp. 147-149, 1998, in "Transversal and Longitudinal Images from the Retina of the Living Eye Using Low Coherence Reflectometry", by A. Gh. Podoleanu, Mauritius Seeger, George M. Dobre, David J. Webb, David A. Jackson and F. Fitzke, published in the Journal of Biomedical Optics, 3(1), pp. 12-20, 1998. En-face OCT allows generation of both B-scan and C-scan (or transversal) images. En-face OCT outputs a reflectivity profile along a trajectory transverse to the optics axis, which we will call it T-scan in the following.

FIG. 1 shows a B-scan image of the cornea made out of several T-scans, a transverse scans, collected at different depths, where the frame duration is the time required for depth advancement and FIG. 2 shows a C-scan image of the cornea by repeating T-scanning along the horizontal X-direction at several Y positions along the vertical coordinate, where the frame duration is determined by the time to advance the vertical position of the scanning beam. Both B-scan and C-scan images are affected by the eye movement. A C-scan, as is known in the art, is an image scan taken in a plane normal to the longitudinal direction (a C-scan has the orientation of an image taken by a microscope or a camera). Due to S/N ratio limitations, OCT cannot operate at video rate and consequently, the eye movements detrimentally affect the accuracy of data collected. The B-scan image is either axially stretched or compressed depending on the axial movement direction relative to the direction of frame scanning.

Similarly, due to movement, the C-scan image shows an external contour of the cornea which differs from a circle. FIG. 3a shows the external contour of the cornea as shown by C-scan images in the center of the cornea at different depths, a<b<c. FIG. 3b shows the external contour of the cornea at depth b while the eye moves axially towards the OCT instrument during the frame scanning duration. The contour in the first top half of the frame follows the correct contour of the circle of radius $R_b$ while in the half frame at the bottom, that of a circle of larger radius, shown as $R_c$ for the case when the eye moved axially to modify the equivalent depth from b to c. FIG. 3c shows the external contour of the cornea at depth b while the eye moves axially away from the OCT instrument. The contour in the first top half of the frame follows the correct contour of the circle of radius $R_b$ while in the half frame at the bottom, that of a circle of smaller radius, shown as $R_a$, for the case when the eye moved axially to modify the equivalent depth from b to a. The central part of the image, which represents scattering points from inside the cornea volume confuses the border detection in the process of drawing a contour over the image. The C-scan image presents a transversal image through the Bowman layer, as the darker area between the external contour (epithelium) and the border of the bright scattering disk in the center of the image. This information has been discarded so far from quantitative evaluations.

As another disadvantage, a single B-scan OCT image displays the curvature along the azimuth angle cut chosen, no information exists in this image on the curvature along other azimuth angle orientations.

FIG. 2 shows an en-face OCT image collected with an OCT system as described in the paper "En-face OCT imaging of the anterior chamber", by A. Gh. Podoleanu, J. A. Rogers, G. M. Dobre, R. Cucu, D. A. Jackson published in the SPIE proceedings, Vol. 4619, 2002, p. 240-243. The image was collected in 0.5 s and in the same time interval, the eye has moved axially towards the scanning head of the OCT and the shape of the external contour of the image deviates from a circle. If only an OCT longitudinal image would have been collected along the cut AA' shown in FIG. 1, then the curvature on the left (about A) would have been less than the curvature of the profile shown on the right (about A'). Obviously, a B-scan OCT image would have come up distorted and provided an incorrect value for the cornea curvature. It would be more difficult on the individual B-scan image to distinguish the asymmetry. This image demonstrates that the asymmetry is easier visible in the C-scan than in the B-scan imaging, however so far C-scans have not been used to assess the cornea curvature.

Axial and lateral movements of the eye during the image acquisition manifest differently in the image depending on the scanning mode, B or C-scan.

Thus, a need exists for a better procedure to evaluate the cornea shape and reduce the effect of the eye movement when using OCT to determine the curvature of the cornea. The method and systems proposed are equally useful for stationary objects, providing the curvature of the object in one or fewer steps than required by the known technologies.

Different methods for measurement of the axial and lateral position of the eye are known, as described in the U.S. Pat. No. 7,113,818. They use position sensors or OCT systems. They are cumbersome, slow and usually, the methods for transversal movement or shift evaluation are different from the method and system to evaluate the axial position. If they are applied in robotics to evaluate the inclination of the object, then different systems implementing different technologies should be combined.

Therefore a need exists for a simpler and faster method and system to provide the axial distance of an object as well as its tilt, using the same and unique measuring technology.

SUMMARY OF THE INVENTION

The present invention solves the above problems by means of a procedure which employs en-face OCT to evaluate the cornea curvature and in a preferred embodiment, the curvature of the cornea as well as the relative axial position of the cornea in respect to a fixed point.

The invention provides a method and apparatus to evaluate at the same time the shape as well as the relative distance of the object from a fixed point. In a preferred embodiment, the method and apparatus measures the axial position of the cornea during patient eye examination and at the same time, the cornea shape.

According to a first aspect of the invention there is provided a method of obtaining geometrical information about an object, comprising transversely scanning the object with an OCT instrument including a low coherence interferometer to obtain an en-face OCT image; introducing differential delays with known values into a path of light, wherein said light passes through said interferometer to produce an output beam comprising multiple parallel beam portions having different path lengths associated therewith, and thereby generating in said en-face OCT image a set of two dimensional image contours at different depths, each said two dimensional image contour corresponding to a said respective beam portion, and said two dimensional image contours having a known depth relationship determined by said differential delays; and computing the geometrical information about the object from at least two of said of said sets of two-dimensional contours in the said en-face OCT image.

It will be understood that the light does not need to be visible light, and the term includes any electromagnetic radiation, such as infrared light, suitable for use in an OCT instrument. It will also be understood that while the light must of course pass through the interferometer, the point in the path where the delay is introduced can either be internal to the interferometer, in the object beam or the reference beam, or outside it, for example in the source path.

It will be understood by one skilled in the art that OCT can be implemented either by flying the spot across the cornea, collecting the signal pixel by pixel, sequentially or by collecting all transverse pixels in parallel by using CCD cameras. The invention is equally applicable to both systems, and the term scan is intended to cover both types of systems.

The geometrical information can be the axial position of the object or the overall three dimensional shape.

The invention generates the image contours at different depths simultaneously so eye movement between images is no longer a problem. The image contours in different image planes may be generated by introducing a multiple delay element in a beam in the interferometer to create different path lengths across the beam. Preferably, the multiple delay element is introduced into the reference beam of the interferometer, although it could equally be introduced into the object beam. This results in different width portions of the beam creating image components at different depths. Of course, it will be understood that the different portions of the beam could be separate beam components bundled together to form a combined "beam" scanning the object. The orientation is not important so long as different portions of the "beam" scanning the object have different path lengths.

The different path lengths are preferably created by introducing a transparent block having a varying thickness across its width into the beam. The thickness preferably varies in a stepwise manner, wherein the steps are of equal height. This ensures that most of the path differences are equal. They are not all equal because the path difference between 0 and the first is path is $2d(n-1)$ and between successive steps it is $2dn$.

However, the differential delays could be made deliberately unequal in order for a standard curvature at a standard axial distance to produce equally spaced contours in the composite C-scan image. In this case, any other curvature deviating from the standard curvature and the object of standard curvature deviating from the standard axial distance will produce contours placed at unequal distances.

It is understood that the word transparent applies in relation to the wavelength of the light used in the OCT instrument.

The differential delays could equally be introduced via optical fibers, using two fiber trees, one to split light into a number of M outputs and a second tree to bring all M outputs of the first tree into the M inputs of the second tree, where the fiber lengths between the two trees are adjusted to implement desired differential lengths.

In order to distinguish the circular contours generated by a delay element in C-scan OCT, the delay introduced by each successive layer in the reference arm should be larger than the coherence length of the source. If this condition is not respected, the thickness of each contour is too large and adjacent contours will merge together.

According to a second aspect of the invention there is provided an apparatus for obtaining geometrical information about a curved object, comprising an OCT imaging instrument for generating a composite C-scan image of the curved object; and said OCT imaging instrument employing a beam including multiple path lengths so as to generate a series of two dimensional image contours in different image planes within the composite C-scan image, said image planes having a known depth relationship determined by the differences in the optical path lengths so as to permit the geometrical information to be computed from the image contours and the known depth relationship there between.

The multiple path lengths are conveniently created by means of a differential multiple delay element inserted in a beam of the OCT imaging instrument.

In another aspect, the invention provides a method based on the combination of the longitudinal and en-face OCT to further enhance the accuracy of the determination.

In yet another aspect, the invention provides a method for determining the axial distance up to the cornea or its curvature by measuring the distance between the epithelium and the Bowman layer in C-scan images collected at different depths.

In yet another embodiment, the invention provides a method to compare and superpose the curvature information onto the C-scan image. This could be the C-scan image obtained with no optical delay element in the interferometer, of the same lateral size as that in the said composite C-scan image. The C-scan image to be used to superpose the curvature information on, or compare the image with the curvature distribution, could equally be obtained by blocking the reference beam and collecting the object beam only, by means reported in the U.S. Pat. No. 5,975,697 and U.S. Pat. No. 6,927,860, and processing sequentially the OCT image and the image obtained after the reference beam was blocked as described in the same U.S. Pat. No. 5,975,697 and U.S. Pat. No. 6,927,860 patents. In this way, the curvature information could be superposed on the C-scan OCT image or with the C-scan image acquired using the aperture in the object arm (termed as confocal channel in the U.S. Pat. No. 5,975,697 and U.S. Pat. No. 6,927,860).

In a different embodiment, the invention refers to a method where the axial distance of the object translates into a transversal distance in the C-scan OCT image. If only axial distance is necessary, a case encountered in eye tracking, then an object with optimum shape can be used, and attached to the sample whose axial distance is to be measured, monitored or tracked. Even more, the scanning regime can be reduced to one transverse coordinate. The invention refers to the design of the most useful shape of the object to achieve a range of axial distances as well as to optimize the sensitivity of the method about certain axial distance values.

In yet in another embodiment the invention provides a method for the lateral alignment of the eye by projecting in the same composite image the endothelium and epithelium of the cornea. In order to achieve such a composite image, a delay element with one step is used with a step delay comparable to the optical delay introduced by the thickness of the cornea and its index of refraction. In this case, lateral alignment could be improved by using the Purkinje reflections (from the epithelium, endothelium of the cornea and from the eye lens).

In a different embodiment, the invention provides for a method to evaluate the orientation of an object and its axial position by inspecting the orientation, transverse position and differential distance between the lines in the multiple grid of lines in the C-scan OCT composite image obtained from a plane surface. The larger the inclination, less is the distance between the lines in the grid, ie the differential distance between the lines reduces with the inclination. The grid in the C-scan OCT image will be oriented diagonally, depending on the magnitude of angles $\alpha$ and $\beta$ which the normal to the plane makes with the optic axis measured in the horizontal and respectively vertical plane.

In summary, the axial distance according to the invention could be inferred from:

(i) number of contours;
(ii) differential distance between contours in the composite C-scan image;
(iii) lateral distance between a reference position of the contours in the C-scan composite image and the current lateral position of the multiple contours.

BRIEF DESCRIPTION OF THE DRAWINGS

Other features of the present invention, as well as other objects and advantages attendant thereto, are set forth in the following description and the accompanying drawings in which like reference numerals depict like elements. Accordingly, various embodiments of the optical mapping apparatus of the present invention will now be described by reference to the following drawings wherein:

FIG. 4a shows a first embodiment of the invention.

FIG. 4b shows a circle approximating the cornea.

FIG. 5 shows the block to provide a plurality of optical delays.

FIG. 8 shows a C-scan obtained from a metal ball using the invention.

FIG. 9 shows a C-scan obtained from the cornea of a volunteer using the invention.

FIG. 10 shows the implementation of a method according to the invention using the Bowman layer.

DETAILED DESCRIPTION OF THE PREFERRED EMBODIMENTS

Figure 1:
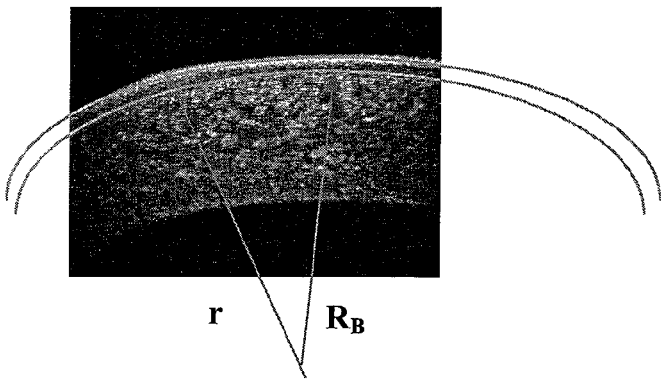
FIG. 1 shows a B-scan OCT image of the cornea obtained from en-face scans.

Various features of the present invention, as well as other objects and advantages attendant thereto, are set forth in the following description and the accompanying drawings in which like reference numerals depict like elements.

An en-face OCT involves and makes use of techniques known in the art and as described in U.S. Pat. No. 5,975,697, Optical mapping apparatus with adjustable depth resolution, and U.S. Pat. No. 6,769,769, Optical mapping apparatus with adjustable depth resolution and multiple functionality. An OCT can be constructed in bulk or optical fiber, has means for transversally scanning the target, has means for longitudinal scanning of the reference path length, has means for controlling the phase and polarization in order to maximize the interference signal, has means to display images. These systems could generate B-scan and C-scan images and could be easily switched from one regime to the other. In a Cartesian coordinate system, where the x-y plane is the plane in which en-face images lie, and the z axis represents the depth direction, B-scans are longitudinal sections in planes such as x-z or y-z planes containing the z axis, and C-scans are tranverse sections in planes parallel to the x-y plane. For those skilled in the art it will be apparent that en-face OCT scans (T-scans) could be collected using linear photodetector arrays and C-scan images by employing one scanner to add the other dimension to a raster image as well as by using CCD arrays without a mechanical or optomechanical scanner. The present invention is equally applicable to such OCT procedures of generating T and C-scans.

In the following reference will be made to procedures where the curvature of the object or cornea is inferred from C-scans.

Figure 2:
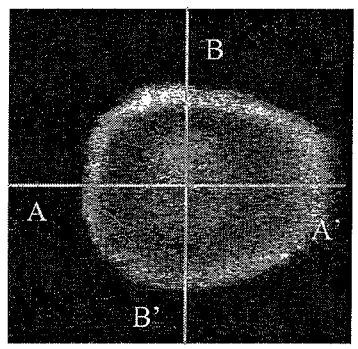
FIG. 2 shows a C-scan OCT image of the cornea obtained from en-face scans.
Figures 3A, 3B, 3C:
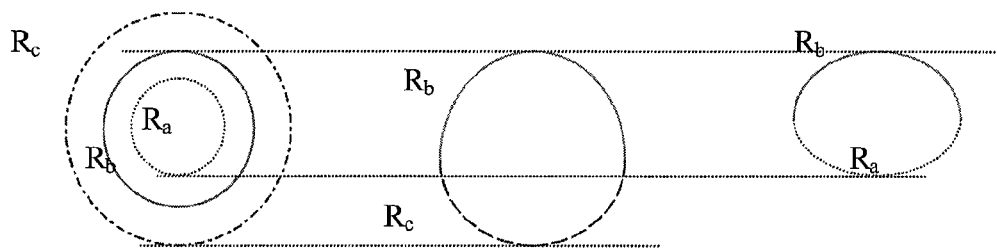
FIGS. 3a to 3c show the effect of movement on the C-scan OCT image.

FIG. 1 shows a B-scan from the cornea of a subject while FIG. 2 shows a C-scan from the same cornea.

Cuts Across an En-Face OCT Image of the Cornea

Two diameters are shown in FIG. 2 over the C-scan image, acquired at an axial position (depth) z. More radial lines can be drawn, two only are shown for brevity. The average of distances AA' and BB' gives an approximation for the diameter, $D(z_i)$ of the circle which can be drawn around the image in FIG. 1. More C-scan images can be acquired at different depths $z_n$ and for each depth, a new value is worked out for the diameter $D(z_n)$. A curve $D(z)$ drawn with the diameter values versus the selected depth, z, in the OCT describes the curvature of the cornea. This procedure requires that a stack of C-scan images is collected. If a frame is obtained in 1 s, then in order to scan 4 mm depth in air with 40 microns, 100 such images are required, so 100 seconds.

Therefore, to speed up the multiple acquisition of the epithelium profiles, at different depths, the following procedure is proposed as described below. This consists in using multiple optical path difference (OPD) values in the interferometer at the core of the OCT system.

An interferometer illuminated by a low coherence source 1 is at the core of any OCT instrument. The interferometer could consist of one or two or several optical splitters, not shown in FIG. 4 but incorporated generally into the block 2. The optical splitters could be single mode fiber couplers, bulk beamsplitters or combination of such elements thereof. The embodiment of the present invention shown in FIG. 4 refers to any configuration of en-face OCT instrument, which can be used to image the cornea, lenses or industrial objects. Any interferometer has an object arm 3 leading to the object under test, 4, and a reference arm, 5, leading to a mirror or re-circulating mirror, 6. Maximum strength interference is produced when the OPD between the object arm and the reference arm is zero. By creating a multi-step OPD, with a suitable step difference in between the individual steps, any en-face OCT image at a certain depth is replicated at a number of path position values, given by the number of steps in the OPD. The multiple steps could be introduced in different ways. As shown in FIG. 4, a block of transparent material, 7 for the wavelength used, such as glass or BK7, is shaped to introduce several path differences in the transverse section of the reference beam. Obviously, the block 7 could be introduced into the object arm as well.

For instance, let us say that the lens or metal sphere or cornea to be measured has a shape bulging out over a D=1 mm depth. N contours can be obtained in an en-face OCT image of the lens if a block 7 with N steps is used. The differential step between the different OPD values should be larger than the coherence length, $l_c$, therefore, the maximum number of steps is $D/l_c$. With a coherence length of 20 μm, up to N=50 values could be used. A block 7 with N=5 steps is shown in FIG. 5. Here each beam traverses a step of height $d_i$, with an area determined by the block width and the lateral size $b_i$.

In this way, a number of contours, close to circles are obtained when imaging en-face the cornea. Knowing the difference in height between the stairs, $d_i$, and the lateral size of the scanning, the curvature of the lens or cornea can be inferred.

Figure 6:
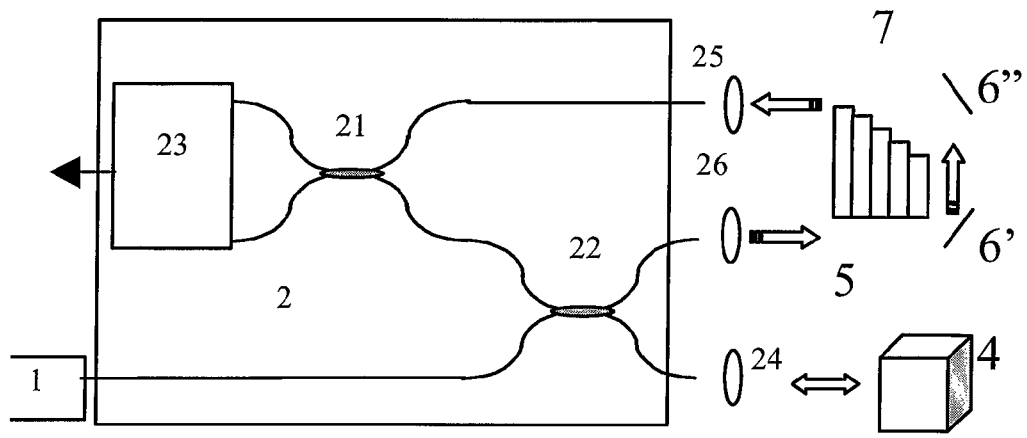
FIG. 6 shows another embodiment of the invention.

In FIG. 4, the differential delay between adjacent beams traversing the block 7 is 2dn as each beam traverses the stair block 7 twice, where n is the index of refraction of the block 7 and all $d_i$ considered equal to a quantity d. Preferably, for better control of the differential OPD step introduced by the stair and control of traversing beam, the interferometer uses a recirculating reference beam, in which case each step of the stair is traversed only once by the beam. Such OCT configurations are known in the art, where the beam is not returned from the launching port but traverses the reference path and lands into a different port, such as in Mach Zehnder configurations. A possible configuration is shown in FIG. 6. Here the interferometer 2 contains two single mode fiber couplers, 21 and 22, the reference beam 5 traverses the multiple delay block 7 and is re-circulated via mirrors 6 and 6' from coupler 21 to coupler 22, terminated on the photodetector 23, part of the OCT interferometer 2.

If the block 7 is used in reflection, then the differential delay is given by the height of the individual stair.

Different parts of the extended beam 5 traverse different lengths of the stepping block 7. Beam 0 is the part of the beam which misses the block 7. The subsequent parts 1, 2, . . . i, N will be consequently delayed by $\delta_1, \delta_1+\delta_2, \ldots, \delta_1+\delta_2+\ldots\delta_N$. In case all differential OPDs are equal, then $\delta_N = N\delta$, where $\delta = 2dn$ in the double path configuration such as that in FIG. 4 and nd in the single path configuration in FIG. 6. Let us consider that the optical heights of block 7 are equal, that the optical path length of the "0" beam is $D_0^r$, and the length of the object arm up to the top of the curved object 4 is $D_0^o$. Then, the other beams will incur path lengths, $D_0^r+\delta n$, $D_0^r+2\delta n$, ... $D_0^r+i n \delta$. The object path up to a scattering point at distance z' inside the object 4 is $D_0^o+n_o z'$, where $n_o$ is the average index of refraction of the object. For simplicity, in the following we consider the distance z measured in air, at the border of the cornea with air, as shown in FIG. 4b.

Using the translation stage 7, the reference length, $D_0^r$, is adjustable in order to scan the depth and produce B and C scan images. M contours are obtained in the C-scan image up to the depth $z_m$ given by:

$$2n_o z_m = D_0^r - 2D_0^o + nm\delta \quad (1)$$

where the $m^{th}$ contour is determined by the $m^{th}$ stair in object 7.

In the particular case of $D_0^r = 2D_0^o$, $z_1 = n\delta/n_o = Z$, $z_2 = 2n\delta/n_o = 2Z$, . . . . . To place all images corresponding to the N different OPD values for all N steps inside the object volume, $D_0^r$ should be equal or larger than the object optical path length evaluated up to the top of the object, $2 D_0^o$:

$$D_0^r \geq 2D_0^o \quad (2)$$

If even the most delayed part of the reference beam does not reach the top of the object in optical path length, then no image will be obtained, i.e. when $$D_0^r + Nn\delta < 2D_0^o - \frac{l_c}{2} \quad (3)$$

where $l_c$ is the coherence length of the source. For values of $D_0^r$ which are larger than the values given by (2), 1, 2, up to N number of contours will be obtained in the image. This shows that depending on the reference path adjustment, $D_0^r$, the number of contours change and that the $m^{th}$ stair determines a contour with the index up to m, when (1) is accomplished.

Figure 7A:
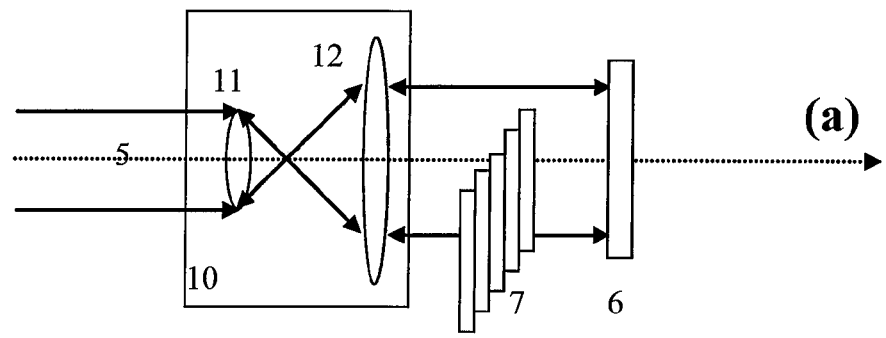
FIGS. 7a and 7b show another embodiment of the block to provide a plurality of optical delays.
Figure 7B:
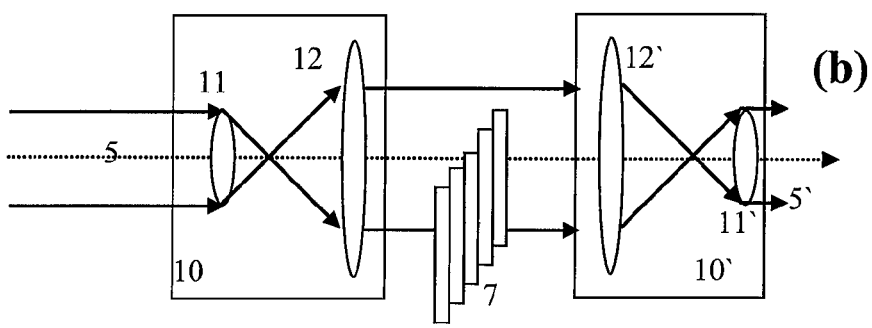

If many steps are required, it may be difficult to construct the block 7 to intercept a small diameter beam. Therefore, it is advantageous to increase the beam diameter, which allows a block 7 of a decent size to be easy manufactured. This could be achieved by incorporating the block 7 between telescopes. Such telescopes are known in the art, using mirrors or lenses, or lenses and mirrors, two lenses are shown in FIG. 7.

The block 7 can be manufactured in different ways, with linear symmetry as shown in FIGS. 4*a* and 5, or radial symmetry, in which case plates are superposed with all corners superposed.

A cone shape for the multiple delay element 7 could also be used in which stares are circularly embossed, oriented normal to the incident beam. To uniform the distribution of power in the plurality of beams, the width of each stair embossed in the cone or the lateral distance between two adjacent slides, when the delay element 7 is made from microscope slides, $b_i$, as shown in FIG. 5, are optimized in such a way as the area of the beam intercepted by each step determining a particular path difference is constant.

In order to generate multiple optical path differences, N microscope slides can be superposed to each other at an angle, in such a way as the areas seen by each part of the beam is substantially the same.

Because power in the beam decreases radially out from the axis, this could be compensated by using increased intercepting areas for the different stairs of the block 7. The width $b_i$ in FIG. 5 could be chosen to vary according to such a law as to intercept areas inversely proportional to the power in the intercepted beam at the off-axis distance where the stair i is placed.

To uniform the distribution of power within the plurality of delayed beams, diaphragms in front of the telescopes in FIG. 7 could be used according to means known in the art. This is however practicable when block 7 is used in the reference beam only and not in the object beam.

The block 7 can be implemented in fibre, with a plurality of single mode fibers with a joint entry and joint exit fiber. As another possibility, a taper form from multiple fibers could be used and shaped in stairs at one output. Different possibilities exist to implement such devices with a plurality of OPDs, in bulk, fiber or other waveguide form. The only requirement is that the plurality of OPD steps is well defined in value, continuous transition from one step to the other is avoided and the differential step is greater than the coherence length of the source. This condition, when met, allows generating sharp distinct contours which subsequently could be distinguished by image processing means, such as border detection or any other means known in the art.

Important when evaluating the curvature of the cornea is that the contours stand out from the scattering centers from within the cornea volume. The signals scattered from points inside the volume generate a diffuse background. In order to enhance the contrast of the contours in comparison to the scattering light from the cornea volume, the invention proposes to use a source whose wavelength is absorbed by the tissue. When examining the cornea, wavelengths absorbed by the water in the cornea are advantageous. In this way, the scattering centers from deep inside the tissue will return less light. Radiation with a wavelength larger than 1 micron encounters significant attenuation in the cornea. Even more, absorption could be advantageously employed. Low coherence sources are now available at a wavelength of 1.4 micron, or at 1.6 microns where the water absorbs more than at 1.3 micron largely used for OCT of the cornea. Other wavelengths can be chosen to coincide with water absorption peaks.

In a different aspect, the invention provides means for measurement of the axial position of the object. As explained above, by bringing the object closer to the system in FIG. 4 or 6, equipped with a block 7 with N steps, the number of contours varies from 1 to N. Knowing the differential OPD between adjacent steps, the axial position of the object can be estimated. If the differential steps are equal, then the number of contours provides a direct reading of the axial position with an error equal to the differential step. This can be used in eye tracking to estimate the instantaneous axial eye position or to eliminate the movement effect.

As an improved procedure for better estimation of the axial distance, if the cornea curvature is known, then for the same number of contours, before one more contour appears or before one more contour disappears, the differential distance between the contours in the image provides information on the eye axial position. This procedure can be used to estimate the axial eye position better than by counting the number of contours in the C-scan. For instance, approximating the cornea shape with a circle of known radius, and knowing the differential delay between steps, equations can explicitly be written for the differential distance between a given circle and the adjacent circle, for instance for indexes, i and i+1, or i and i+j, with any value for j from 1 to the number of circles. Although the steps in block 7 are equal, the differential distance between contours is different due to the cornea curvature. If the object investigated would be a cone, then the differential distance between neighbouring circles would be a constant. In principle, if the curvature and the index of the circle are known, then the axial distance could be estimated by measuring the radius of the circle.

The axial distance up to the object can also be inferred from the lateral distance between the center of the circles and the first circle in the composite C-scan OCT image.

FIG. 8 shows such contours obtained from a metal sphere of 22 mm diameter and for different OPD values, where zero OPD corresponds to the situation when the top of the sphere is seen in the C-scan OCT image as a blob in the center. 4 microscope slides of 200 micron thickness have been used to construct the block 7.

FIG. 9 shows similar contours from the cornea of the author. Approximating circles are drawn above the same contours in the right columns of FIGS. 8 and 9.

In the first and second raw in FIG. 8, the OPD is such as less than 4 circles are shown (intermediate situation between equations 2 and 3. 4 circles are shown in the $3^{rd}$ raw (equation 2 accomplished).

The procedure for evaluating the cornea curvature proceeds in the following steps.

Adjustment phase
1. The patient is adjusted horizontally and vertically on the axis of the scanning head. Then, $D_0^r$ is decreased and $D_0^o$ is increased until first contours appear in the image. The adjustment of $D_0^r$ and $D_0^o$ continues until maximum such number of contours are obtained in the C-scan image.

Imaging Phase
2. Using apparatus show in FIG. 4*a*, for example, several en-face OCT images of the cornea are acquired for different relative distances of the eye to the scanning head, which randomly varies due to the eye movement.

Processing Phase
3. Several images with the most symmetric contours, undistorted by blinks and minimally distorted by eye movement are selected and transferred to a storage unit.

4. By software means, the contours are edge detected and their shape approximated with circles. Then the diameter of each such circle is estimated.
5. For each circle of radius R, approximating the shape of the cornea with a circle of radius r, an equation can be written involving the arbitrary $OPD_0 = D_0^r - 2 D_0^o$ (for the set-up in FIG. 6 for instance), r, and δ. Using two such circles, the two unknowns, $OPD_0$, and r can be uniquely determined.
6. The procedure at 4 is repeated for the next two neighboring circles which output values for the two unknowns, z, and r, or using any other pair of circles.
7. Many such sets could be obtained using the average diameters for the circles, and then averages of the values z and r are calculated.

Those skilled in the art will appreciate that different other combinations of equations can be used, for instance using the equations for the circles at 2δ, or 3δ or any other combinations.

In general, using the contour of the circle of radius R approximating the cornea shape, approximated as part of a circle of radius r in FIG. 4b, we can write:

$$R^2 = r^2 - (r-z)^2 \quad (4)$$

where z is the distance from the top of the cornea up to the intersecting plane determined by the coherence gate.

Let us consider the case when $D_0^r = 2D_0^o$ and the differential axial distance Z between the successive planes determined by the coherence gate for the succession of steps in the block 7, the contours could be approximated with circles of radius $R_i$, where:

$$R_1^2 = r^2 - (r-Z)^2 = 2rZ - Z^2 \quad (5)$$

$$R_2^2 = r^2 - (r-2Z)^2 = 4rZ - 4Z^2 \quad (6)$$

$$R_3^2 = r^2 - (r-3Z)^2 = 6rZ - 9Z^2 \quad (7)$$

etc. Each equation alone can be used to determine a value for the cornea curvature, r. If the distance z differs from exact integer numbers of Z, let us say by ϵ, then the equations above become:

$$R_1^2 = r^2 - (r-Z-\epsilon)^2 = 2rZ - 2r\epsilon - Z\epsilon - Z^2 - \epsilon^2 \quad (8)$$

$$R_1^2 = r^2 - (r-2Z-\epsilon)^2 = 4rZ - 2r\epsilon - 4\epsilon Z^2 - \epsilon^2 \quad (9)$$

$$R_1^2 = r^2 - (r-3Z-\epsilon)^2 = 6rZ - 2r\epsilon - 6z\epsilon - 9Z^2 - \epsilon^2 \quad (10)$$

The first two equations can be used to determine one set of values for r and ϵ, the second and the third equations can be used to determine a second set of values for r and ϵ and so on. The axial distance results from the number of circles corrected by the ϵ value.

Any other pairs of equation could also be used to obtain values for r and ϵ.

A histogram of values r versus z can be obtained to represent a variation in the cornea curvature, or an average of all r values can be produced as an estimate for the cornea curvature, r.

The example above where we approximated the contous with circles is valid as long as the object is spherical. In reality, the cornea admits polar variations of the curvature and therefore more evolved shapes for the contours should be used than circles, for better fitting and parameter evaluation. Let us now consider that the curvature depends on the polar angle, θ, as shown drawn for the last image in FIG. 9. For each angle θ, a pseudo-diameter $2X_m(\theta)$ replaces the diameter of the circle considered before. Let us consider that the reference path with no MDE is adjusted as to select a depth z from the object.

Then, by introducing the MDE which generates Z differential distance between the planes selected by the different delay steps in the MDE 7, a number of contours are generated due to superposition of C-scans within the one frame compound image, one for each depth generated by each step of the MDE.

For contours p and m $$r^2 = X_p^2 + [r-z-(p-1)Z]^2 \quad (11)$$

$$r^2 = X_m^2 + [r-z-(m-1)Z]^2 \quad (12)$$

These equations can be rewritten as:

$$\sqrt{r^2 - X_p^2} = r - z - (p-1)Z \quad (13)$$

$$\sqrt{r^2 - X_m^2} = r - z - (m-1)Z \quad (14)$$

By deducting the two:

$$\sqrt{r^2 - X_p^2} - \sqrt{r^2 - X_p^2} = (m-p)Z \quad (15)$$

By two successive squares applied to the above equation:

$$r = \frac{\sqrt{(X_p^2 - X_m^2)^2 + 2(X_p^2 + X_m^2)(p-m)^2 Z^2 + (p-m)^4 Z^4}}{2Z \operatorname{Mod}(p-m)} \quad (17)$$

where Mod means the modulus of the difference p−m.

Using different contours p and m, all values obtained should oscillate about the real value r.

Because the radius values are evaluated along a polar orientation θ, $$r_{p,m}(\theta) = \frac{\sqrt{\begin{array}{c}(X(\theta)_p^2 - X(\theta)_m^2)^2 + 2(X(\theta)_p^2 + X(\theta)_m^2) \\ (p-m)^2 Z^2 + (p-m)^4 Z^4\end{array}}}{2Z \operatorname{Mod}(p-m)} \quad (17)$$

An average over all pairs of contours p and m $$r(\theta) = \langle r_{p,m}(\theta) \rangle_{p,m} \quad (18)$$

can be estimated to obtain the curvature r at the polar angle θ.

The evaluation of distances $X_m$ along polar direction θ represents an improvement for the step 4 above in the imaging phase.

The depth z can also be obtained from any of the equations (11) or (12) above:

$$z_m(\theta) = r - (m-1)Z - \sqrt{r^2 - X_m^2} \quad (19)$$

where the subscript m means the depth, z, as determined from the contour m using the curvature r. This could be and approximated with:

$$z_m = r - (m-1)Z - \sqrt{r^2 - \langle X_m^2 \rangle_\theta} \quad (20)$$

where a circle is fitted to the contour, of radius $R = X_m$.

As a better estimate, a value $$z = \langle z_m \rangle_m \quad (21)$$

as average over all m contours with m from 1 to N could be obtained.

All values $z_m$ should oscillate about z.

The example above shows that the curvature, $r(\theta)$ and the distance, z, can be determined from the polar distances $X_p$ shown in FIG. 9 bottom.

Those skilled in the art could realize that equivalently, equations could be written to obtain values for the curvature $r(\theta)$ considering the relative distance between $X_p(\theta)$ and $X_{p+j}(\theta)$, for different values of j between 1 and N number of contours.

Astigmatism and other aberrations of the object shape can be evaluated by fitting splines or Zernike polynomials to the resulted contours in the composite C-scan image.

By adjusting the distance, $D_0{}^r - 2 D_0{}^o$, the number of contours in the image varies from none to N, and that adjustment is preferred which determines a large numbers of contours, slightly smaller than the maximum number by 2 or 3 units, to allow for eye movements. If the adjustment which determined N contours to be seen is selected, then accidental eye movement towards the system leads to the central part of the cornea not being sampled by any contours, while N contours are still obtained from larger depths. However, the errors in estimating the curvature and axial depth increase as contours are moved to deeper positions.

In a different aspect, the invention provides an improvement in the curvature determination of objects by comparing or averaging results obtained in both regimes of operation, B and C-scan. An OCT system similar to that in FIGS. 4 and 6, but without the block 7 is used, as known in the art of OCT. The novel procedure consists in imaging the object or the cornea in both regimes, B and C-scans, collecting data on the curvature and then compounding the results for improved accuracy.

B-scan images can be obtained at different polar orientation, determined by the angle θ (this angle is 90° in FIG. 2, where two diameters are shown only). By edge detection or other software means, the epithelium is distinguished. A contour is fitted to the epithelium and the distance $2X_p(\theta)$ determines the cornea curvature, $r(\theta)$, at the angle θ. The curvature of the cornea is approximated by the average, <r>, of all radiuses $r(\theta)$. For better characterisation, a spline or Zernike polynomials could be used instead of a circle, which may indicate different curvatures of the cornea, r, on the left and right hand side of the axis.

Even more a discrete set of B-scan images is generated using an OCT system with no MDE block, at polar orientations, θ, chosen by the user. The curvature could clearly be inferred from each image, however at the selected polar angle θ only.

Collecting a stack of C-scans at different depths using and OCT system with no MDE, allows curvature determination at any polar angle value, θ, however the profile is determined from sampled points at discrete values determined by the selected depths where the C-scans are sampled. This shows that there is scope in cumulating the information acquired using the two regimes of operation, B and C-scan. Additionally, by performing measurements in both regimes, the effect of movement is reduced not only due to the increased amount of data, but because the movement affects the B-scan and the C-scan images in different ways. On each C-scan, a circle is fitted and its average radius, <R> obtained. A curve <R>(z) can be inferred from the stack of images at different depths. More precisely, an ellipse, a spline or Zernike polynomials is fitted to each contour of the C-scan image of the object (cornea) as a better approximation. Astigmatism of the cornea could in this way be determined.

In a preferred embodiment, the method according to the invention, proceeds in the following steps:
1. A single C-scan compound image is acquired using the apparatus shown in FIG. 4a;
2. Polar diameters $2X_m$ along axes oriented at different angle θ are determined for all contours m, with m form 1 to N. Then the radius $r(\theta) = <r_{p,m}(\theta)>$ is determined using equations (17) and (18).
3. Axial position is also estimated using equation (19), (20) or (21).

In a different embodiment, the steps above could be repeated for different depth selected using the optical path selector in the OCT system, and an average of the r values worked out from the r values obtained for each set of contours as explained above.

Better, accuracy of curvature measurement could be improved by combining measurements collected with the system in FIG. 4a but operating in both scanning regimes, B and C. In this case, as a simplified example, the method according to the invention, proceeds in the following steps:
1. A stack of C-scan images at different depths is acquired using the apparatus shown in FIG. 4a;
2. Approximating circles or ellipses, or splines, or Zernike polynomials are drawn around the contours of the cornea, defined as the interface between air and corneal epithelium, and their diameters or respective lengths, 2X, along principal axes are determined. For instance, in case circles are used, a circle of radius D/2 is fitted to approximate the external contour of the cornea in the en-face C-scan and considering the distance z in FIG. 4b, for each depth a cornea radius of curvature is determined as:

$$r_z = \frac{4z^2 + D_z}{8z}$$

and the final curvature radius is determined as the average of radiuses $r_z$.
3. A first intermediate value for the curvature of the cornea is evaluated from the curve diameter versus depth or first intermediate values of curvatures are evaluated from the curve of length along each ellipse axis versus depth when the shape is approximated with an ellipse. For each C-scan, a diameter, $D_z$ is obtained as an average of the length of segments inside the cornea shape measured along radial lines at different angles θ drawn across the cornea shape, all lines crossing an imaginary center approximately placed in the center of the cornea shape or a center determined as the weighting center of the cornea shape.
4. A stack for B-scan images at different polar orientation θ is acquired;
5. Approximating the shape of the B-scan images with circles or splines, or other shapes, circles of different radius are fitted to the cornea shape until the best fit is obtained, tested with mathematical algorithms known in the art.
6. A second intermediate value of the cornea is inferred at different polar angles.
7. If the ellipse approximation is suggested by the processing of the stack of C-scans, then preferably, polar axes orientations are chosen along the principal axes of the ellipses so determined. B-scan are acquired along the new polar angles.

The curvature values obtained from the measurements performed on the first batch of C-scans are averaged with the curvature values obtained from the second batch of measurements using stacks of B-scan images. The method could be improved if instead of the diameters, D, of the circles approximating the contours, polar distances X are used.

In a different embodiment, it is also possible to obtain the C-scan images sequentially without using the multi-element delay.

In yet another aspect, the invention provides means to measure the curvature of the cornea or its axial distance in one shot, using a single C-scan obtained with an en-face OCT system such as that in FIG. 4 or 6 without the block 7, which can be temporarily removed. In this case, the distance between the epithelium in the C-scan image collected from the cornea at any depth and the projection in the C-scan of the Bowman layer serves as indication of either the cornea curvature or of the actual depth in the cornea if its curvature is known.

To obtain the image in FIG. 2, the optical path difference in the interferometer was adjusted slightly inside the cornea, for a distance z approximating the depth of the Bowman layer in FIG. 1 measured in the center of the cornea. FIG. 2 shows the depth of the Bowman layer projected in the C-scan, i.e. along an orthogonal direction to depth. The difference between the external contour drawn around the epithelium and the blob in the center depends on the cornea curvature.

The images in FIGS. 1 and 2 have been obtained at 1300 nm. If the optical source used would have emitted close to an water absorption peak, such as close to 1.4 microns or 1.6 microns or any other wavelength where water absorbs strongly, then the B-scan image in FIG. 1 will fade in depth and the blob in FIG. 2 will disappear, if the depth was larger than the Bowman layer depth.

An axial tracker can be constructed by means known in the art to maintain the C-scan image in FIG. 2, in which case the axial position is maintained within a distance error comparable to the Bowman layer depth, ie 10-30 microns. Considering the depth z in FIG. 4b smaller than the Bowman layer depth, η, the disk in the C-scan OCT image generated by the cornea epithelium is described by a radius:

$$R_E^2 = r^2 - (r-z)^2 = 2rz - z^2 \quad (22),$$

as shown in FIG. 10 left.

The Bowman layer thickness η acts as the steps of the object 7. If z>η, two contours are seen in the C-scan image in FIG. 10b. Approximating this contour with a circle of radius $R_B$ for the Bowman layer:

$$R_B^2 = 2(r-\eta)z - z^2 \quad (23).$$

Equations 22 and 23 can be used to obtain the two unknowns, z and r using the measured values η, $R_B$ and $R_E$.

If however the curvature r is known, distance within the interval η can be monitored by using the equation (4). If the distance is higher than η, then by combining the two equations (22) and (23), the following approximating equation is obtained:

$$z \approx \frac{R_E^2 - R_B^2}{2\eta} \quad (24)$$

This shows how the distance z can be estimated using the Bowman layer thickness, η.

It will be apparent to those skilled in the art that the method using the Bowman layer and the epithelium could be combined with the method using an MDE with multiple steps for better accuracy. In the same spirit, the number of steps in the MDE to achieve a desired accuracy could be reduced by counting on the differential delay introduced between the epithelium and the Bowman layer. Even more, the two contours corresponding to the epithelium and the Bowman layer could be combined with a contour from the endothelium by using a one step delay element with sufficient delay to bring the contour from the endothelium in the same C-scan with the contours from the epithelium, or within the same C-scan using the epithelium and the Bowman layer contours, in case these two layers are used. As the cornea has a thickness of 0.5 mm, considering its index of refraction, a one step delay element of 0.7 mm could bring the endothelium in the same C-scan with the epithelium. Once these two contours are in the same C-scan, in addition to cornea curvature and, or axial distance measurement, lateral alignment of the eye could be performed by aiming to the contours from the epithelium and from endothelium appear circular and concentric.

The contours for the epithelium and endothelium could be correlated for symmetry with Purkinje reflections from the anterior chamber for enhanced accuracy in aligning the eye transversally. In order to superpose the Purkinje reflections to the OCT composite image, the signal from the OCT photodetector could be superposed to the OCT image. If a balance detector is used, then a summation of the two photodetected signals will eliminate the OCT signal and produce an intensity channel which could be used to be displayed at the same time with the OCT image in a separate image or within the same composite C-scan image. If a full field OCT system is used, then the sensor array image already has the image of the cornea including the Purkinje reflections. This image is normally discarded in the process of constructing the OCT image. Therefore it is very simple to add this image to the en-face OCT image.

Alternatively, in a flying spot OCT system, a separate confocal channel could be provided, similar to configurations described in the U.S. Pat. No. 5,975,697, which generates a confocal image in pixel to pixel correspondence to the OCT image, which could be superposed to the OCT image and guide the lateral adjustment of the eye until the Purkinje reflections are in the center of the epithelium and endothelium contours.

The same procedure described above for the cornea is applicable to a lens or any transparent curved object, where the epithelium is replaced with the front surface of the lens and the endothelium with the back surface of the lens. In this case, the extra delay introduced by the one-step delay element 7 should be commensurate with the optical delay introduced by the lens thickness and its index of refraction.

The foregoing description has been presented for the sake of illustration and description only. As such, it is not intended to be exhaustive or to limit the invention to any precise form disclosed. For example, modifications and variations are possible in light of the above teaching which are considered to be within the scope of the present invention.

For instance, the en-face OCT system could be a full field OCT, which collects images using a CCD camera with no beam scanning. The reference beam and the object beam are superposed on the CCD camera and using phase shifting interferometry principle, where at least 3 frames for different OPD values are acquired, en-face OCT images are produced.

Figure 11:
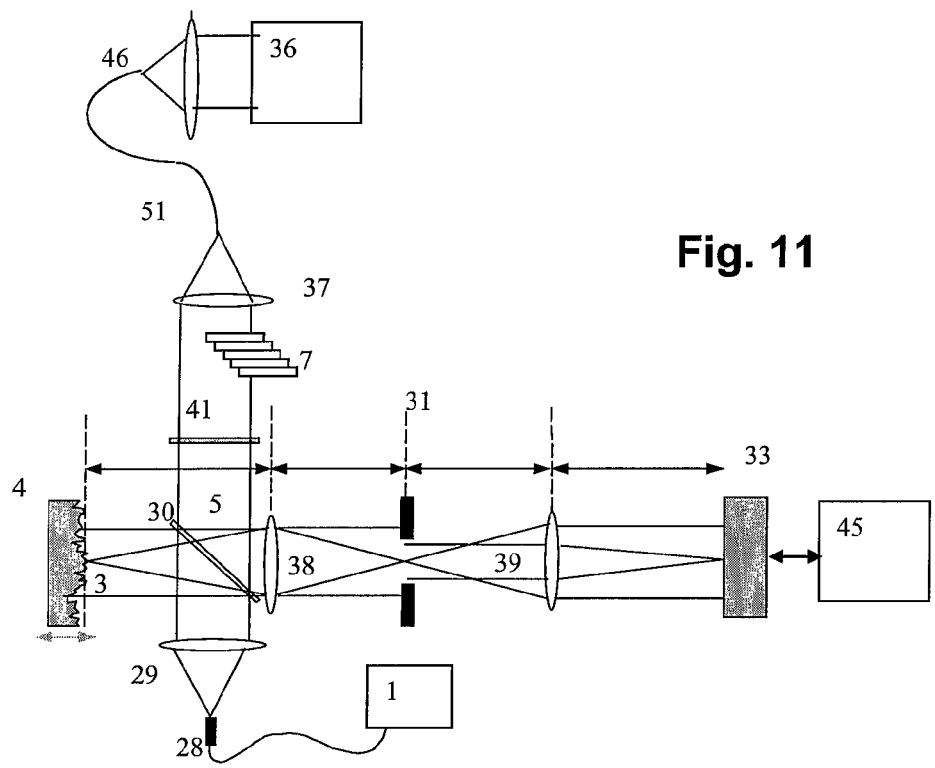
FIG. 11 shows an embodiment of the method using full field OCT.

An OCT system based on the full field principle or coherence radar is known in the art. With reference to FIG. 11, light from the fiber source 1 is launched from the fiber end 28 via lens 29 into a Michelson interferometer, which contains a beamsplitter 30, which splits the incoming light into an object arm, 3, and a reference arm 5. Light returned from the object, 4, via the object arm and from the reference arm via the beamsplitter 30 superposes on the CCD camera 33. The two beams are conveyed to the CCD 33 via a telecentric optic block, using lenses 38 and 39 and spatial filter, such as a pinhole, 31. Because the multiple delay element 7 splits the beam in the reference path 5 in transversal section, which may impact different pixels of the camera in their optical path difference, the light from the multiple delay element is launched via lens 37 into a single mode fiber, 51, which then is launched into the reference path by a lens 46. Because the fiber 51 introduces dispersion, a dispersion compensating element, 36 is required in the reference arm. The dispersion compensation could be achieved by means known in the art using a reflective spectral scanning delay line. This uses a diffraction grating, a lens and a tilted mirror, as disclosed in the U.S. Pat. No. 611,645, Grating based phase control optical delay line by, G. Tearney, E. Bouma, J. Fujimoto and in the U.S. Pat. No. 6,421,164 by, G. Tearney, "Interferometeric imaging with a grating based phase control optical delay line", U.S. Pat. No. 6,282,011B1.

To control the saturation of the CCD 33, a neutral density filter, 41, is used in the reference path 5.

Figure 12:
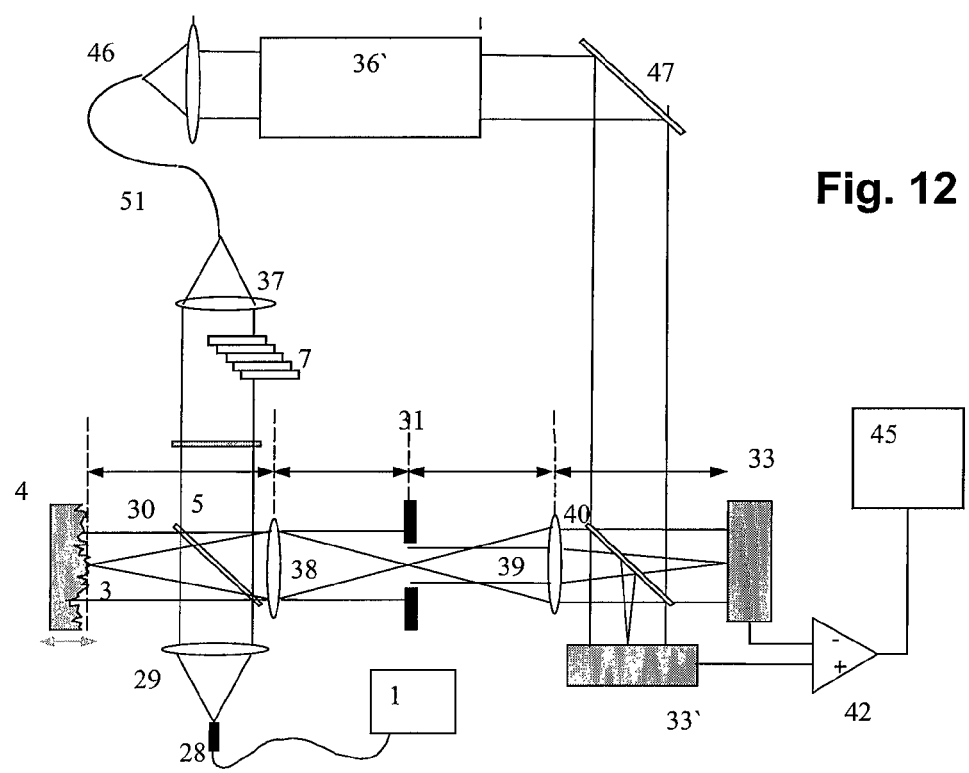
FIG. 12 shows another embodiment of the method using full field OCT.

Alternatively, the reference arm could be prolonged towards the CCD camera via a mirror 47 in a configuration such as that in FIG. 12, where now the element 36' is a spectral scanning delay line in transmission as that disclosed in the United States Application 20060055938.

The object beam and reference beam combine on the beamsplitter 40. One or two cameras, 33 and 33' could be used in a differential balanced configuration, followed by a differential amplifier 42. This has the advantage of elimination of the ambient light contribution and of some of the vibration and noise. The signal from 42 feeds an imaging instrument, 45, such as a digitizer or a frame grabber.

The phase shift delays to demodulate the image could also be introduced using the block 36 in FIG. 11 or 36' in FIG. 12.

Another alternative when using a full field OCT set-up is to construct the multiple delay element from highly parallel microscope slides intercepting all the beam and the differential delays created by multiple reflections between the slides.

Also, the inference of curvature and of the axial position may proceed according to means known in the art by fitting polynomials to the contours in the compound C-scan image, for instance such as Zernike polynomials.

Figure 15:
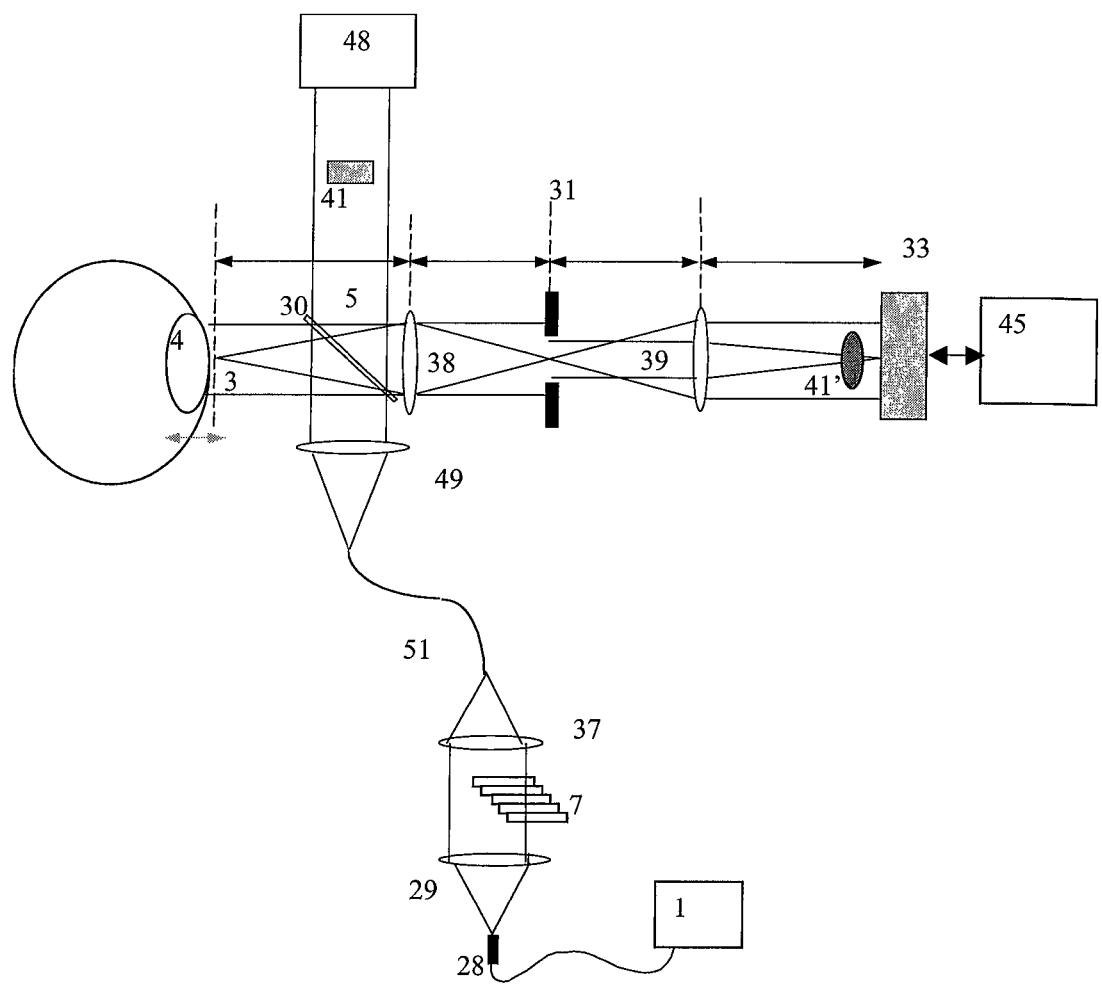
FIG. 15 illustrates an alternative embodiment of the invention where the multiple delay element is added in the source path.

In another embodiment shown in FIG. 15, the delay element 7 and fiber 51 are interleaved in the source path. The source beam from light source 1 is launched into collimating arrangement of lenses 29, 37 to widen the beam so that it can accept the delay element 7, which extends partway across the beam.

On leaving the lens 37, the beam, which now consists of light that is differentially delayed across its width, is launched into the interferometer through lens 49. Because the multiple delay element 7 splits the beam in transversal section, which could thus impact different pixels of the camera in their optical path difference, the light is first launched into single mode fiber 51.

Introducing the delay element in the source beam has a similar effect to introducing it in the reference or object beam. Why this so can be understood as follows. Assume that that the source sends two rays, R1 and R2, with a relative delay d. In the interferometer, ray R1 splits into two, in the object and reference beams, forming rays R1$o$ and R1$r$. Ray R2 also splits into object and reference beams 2R$o$ and 2R$r$.

Rays R1$o$ and R1$r$ will coincide in coherence at zero optical path difference, and rays R2$o$ and R2$r$ will coincide in coherence at zero optical path difference. Now if the interferometer introduces a delay D by having the objet path longer than the reference path, ray R1$o$ will interfere with ray R2$r$ when the total delay is zero as the delay in the source is compensated in the interferometer.

Interleaving the multiple delay element in the source path as shown in FIG. 15 has two advantages:

1. In the case the OCT system used is a full field, as shown in FIG. 11, then no dispersion compensation is required, and the reference path can use a free space path terminated on a mirror 48, as shown in FIG. 15.

2. For a number of delays, n, 2n+1 contours are obtained in the final image.

The multiple path delays introduced into the source arm, before the interferometer work as well with a flying spot instrument as that in FIG. 6, where the 2D en-face images are obtained point by point using a transversal 2D scanner between the output of splitter 22 and the object 4. The same is valid when using a 1D CCD camera, 33, in FIG. 11, 12 or 15 when a line is projected on the object 4 and a 1D transverse scanner is required only, to produce the frame, placed between the splitter 3 and the object 4.

Of particular interest when imaging the cornea is that there is a strong reflection from the apex. To this goal, a neutral density filter, in the form of a disk smaller than the beam diameter may also be introduced in front of the camera, 41', to obscure only the central part only. In this case, no contours can be collected from the central part of the cornea. If that is still desirable, as well as imaging the central part of the cornea, then a neutral density filter with a corresponding radial attenuation can be used, in which case the central part of the cornea is not totally obstructed.

Alternatively, in order to ensure a good visibility across the image, specific for the full field principle, the neutral density filter 41 may radially alter the distribution of the beam in the reference path to match the distribution of the sensitivity with radius when imaging the cornea. Further on, two such neutral density filters could be used, one in front of the camera, 41' and another one, 41, in the reference beam.

The same principle of operation described above in using an OCT systems with a MDE could be applied to track the axial position of a sample by using a special shape devised object to be used in the object beam. This specially devised object is then attached to the sample whose axial position is to be monitored. A cone is better suited than a sphere and even better, a plane which is tilted in relation to the optic axis along a direction which preferentially makes 90 degrees with the direction of line scanning. In this way, a number of horizontal lines are obtained and their number or their position is easier tracked than that of circles. The number of contours along the frame direction in one single frame, or the position of the bunch of contours in respect to a coordinate along the frame direction is a direct indication of the axial position during the frame acquisition.

This refers to a method according to the invention where the axial distance translates into a transversal distance. If only axial distance is necessary, a case encountered in eye tracking, then an object with optimum shape can be used, and attached to the sample whose axial distance is to be measured, monitored or tracked. Even more, the scanning regime can be reduced to one transverse coordinate. For instance, the object could be a cone. In this case, irrespective of the axial position, the differential delays between the contours in the composite C-scan are the same.

Figure 13:
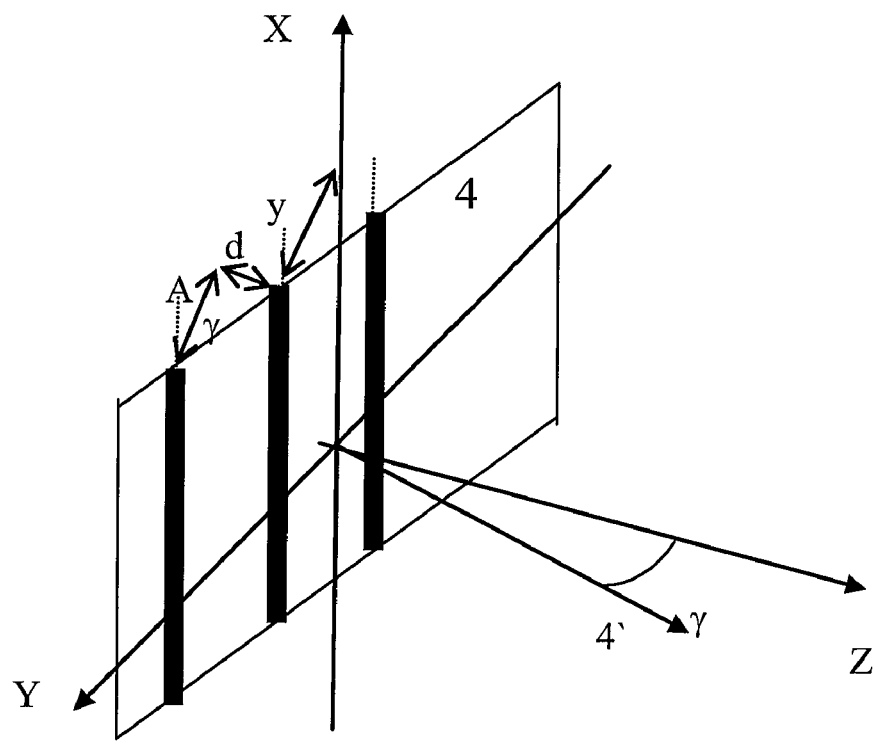
FIG. 13 illustrates the principle of detecting the axial distance.

Because counting contours require border detection and finding the center of the contours, elliptic contours are more difficult to process than line contours. For instance, drawing a line over the multiple contours, depending on the position of the cut, it may intersect the contours at different angles, which lead to the intersecting patches having different areas. Large areas mean reduced accuracy. A line at 90 degrees drawn over a grid of lines looks better suited for the task of axial distance measurement. Such a line will intersect the lines in the grid at the same angle irrespective of its transverse position. Also, equal areas of the intersections between this line and the grid of lines result. Therefore, to produce linear contours, a simple plane slope could be used as an object, as shown in FIG. 13. Let us consider a plane surface, as the object 4, with the normal making the angle $\gamma$ with the optic axis, Z, in the horizontal plane. In FIG. 13, a multiple delay element with two steps is used which generates 3 delays, so three contours, in the case of the plane object, the contours being vertical straight lines in the C-scan image. The thick vertical lines are the C-scan images superposed in FIG. 13 over the object plane 4. The vertical linear strips are distanced apart by A, where A is given by:

$$\tan\gamma = \frac{d}{A} = \frac{l_c}{g_y} = \frac{z}{y} \quad (25)$$

where d is the axial difference in the OPD between successive delays determined by the multiple delay element 7. The width of the vertical line in the image is $g_y$, determined by the angle $\gamma$ and the coherence length, $l_c$. If the angle $\gamma$ is zero, then the fringe pattern is one line covering all object 4, either dark or bright.

The axial position, z, could be inferred from either the number of the lines in the C-scan image or from the lateral position, y, of these lines in the C-scan image. Actuating on the angle $\gamma$, different sensitivity and depth range are achievable. The larger the angle $\gamma$, the lower the sensitivity, but larger the depth range, $\Delta z$ for a lateral size of the object 4, $\Delta Y$:

$$\Delta z = \Delta Y \tan\gamma \quad (26)$$

Even simpler, the XY scanning regime could be reduced to 1D along the horizontal. In this case, the raster is reduced to one horizontal line and the number of peaks in the scanned line, or their temporal position measured from the start moment of the line leads to the axial position of the object.

Figure 14:
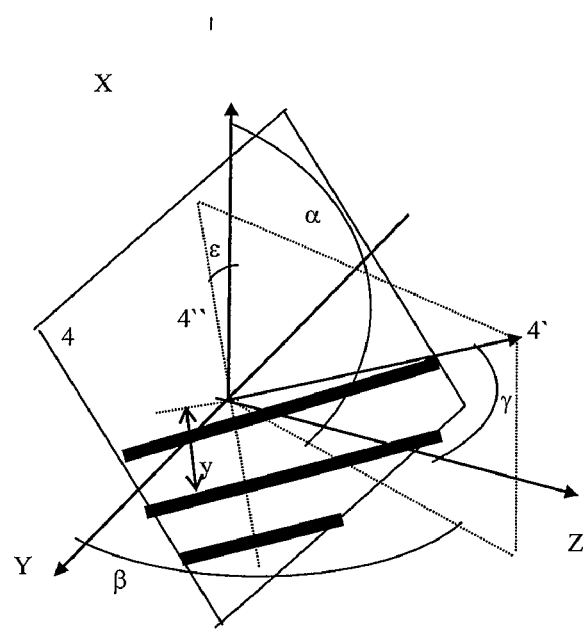
FIG. 14 illustrates the principle of detecting the axial distance and the tilt of the object.

In a different embodiment shown in FIG. 14, the invention provides for a method to evaluate the orientation of the object and its axial position by inspecting the orientation and transverse position of the multiple grid of lines in the C-scan OCT composite image obtained from a plane surface. Let us say that M delays are provided in the OCT system and the object is a plane diffuser. If the normal to the object makes an angle $\alpha$ with the optic axis in the horizontal plane, then M vertical lines are obtained in the composite C-scan OCT image. If the axial position changes, the M lines in the C-scan image will move to the left and right and the horizontal size of the object will determine the range of the axial distance to be measured. The larger the inclination of the object in the horizontal plane, the denser the bunch of lines in the grid, ie the differential distance between the lines reduces with the inclination $\gamma$.

If the normal to the object makes an angle $\gamma$ with the optic axis within the vertical plane, then M horizontal lines are seen in the C-scan OCT image. The vertical position of the M-lines will depend on the axial position of the object.

The larger the inclination of the object in the vertical plane, the denser the bunch of lines in the grid, i.e. the differential distance between the lines reduces with the inclination $\gamma$.

Let us now consider a general angle $\gamma$ of the plane 4 with the optic axis, Z. The grid in the C-scan OCT image will be oriented diagonally, where the perpendicular to the grid of lines, 4" makes an angle $\epsilon$ measured in the plane XY, with the axis X. The grid of lines is perpendicular to the normal, 4' to the plane 4. The distance A measured along a normal, 4", to the grid of lines in the plane XY continues to be determined by equation ( ). The cosine directors of the normal 4' to plane 4 are cos $\alpha$, cos $\beta$ and cos $\gamma$, These are connected to the angles $\epsilon$ and $\gamma$ by:

$$\cos\alpha = \sin\gamma\cos\epsilon \quad (27a)$$

and $$\cos\beta = \sin\gamma\sin\epsilon \quad (27b)$$

When the two cosines $\alpha$ and $\beta$ are equal, then the grid of lines makes an angle $\epsilon = 45°$ in the C-scan composite image. Increasing the tilt $\gamma$ will lead to reduction of the distance A between the grid of lines as seen in the composite C-scan OCT image.

In summary, the axial distance according to the invention could be inferred from:
 (iv) number of contours;
 (v) differential distance between contours in the composite C-scan image;
 (vi) lateral distance between a reference position of the contours in the C-scan composite image and the current lateral position of the multiple contours.

It may also be possible to devise the object 4 from planes of different slopes. This will determine higher sensitivity in tracking the axial position when the bunch of contours slide over small slopes and smaller sensitivity, but larger range when the bunch of contours slide over high slopes.

All references mentioned above are incorporated herein by reference.

I claim:

1. A method of obtaining geometrical information about an object, comprising:
    transversely scanning the object with an OCT instrument including a low coherence interferometer to obtain an en-face OCT image;
    introducing differential delays with known values into a path of light, wherein said light passes through said interferometer to produce an output beam comprising multiple parallel beam portions having different path lengths associated therewith, and thereby generating in said en-face OCT image a set of two dimensional image contours at different depths, each said two dimensional image contour corresponding to a said respective beam portion, and said two dimensional image contours having a known depth relationship determined by said differential delays; and
    computing the geometrical information about the object from at least two of said of said sets of two-dimensional contours in the said en-face OCT image.

2. A method as claimed in claim 1, wherein said path includes a source path extending from a source to the interferometer, an object path, and a reference path, and said differential delays are introduced into said source path.

3. A method as claimed in claim 1, wherein said image contours are located on surfaces that are located at fixed distances apart in the depth direction.

4. A method as claimed in claim 1, wherein a differential delay element is introduced into said path to incrementally vary the optical path length of said sub-beam portions.

5. A method as claimed in claim 1, further comprising temporarily removing said differential delay to create full OCT en-face image of said object.

6. A method as claimed in claim 1, wherein said differential delay is provided by a differential delay element in the form of a transparent block partially intercepting the path of light and having a graduated or stepped increase in thickness across its width, wherein the individual steps are larger than the coherence length of the light used to obtain the images.

7. A method as claimed in claim 6, wherein the differential delay element is adjusted to intercept the beam such that the portions of the beam having different optical path lengths have a uniform intensity.

8. A method as claimed in claim 1, wherein said geometrical information is the external shape of the object or axial position of the object.

9. A method as claimed in claim 1, wherein a delay element is inserted into a collimated portion of a beam of said light.

10. A method as claimed in claim 1, wherein a polar value for the curvature of the said object, $r_{p,m}(\theta)$, is obtained from polar radial distances, $X(\theta)_m$ and $X(\theta)_p$ evaluated along a polar orientation $\theta$ in the said composite C-scan OCT image:

$$r_{p,m}(\theta) = \frac{\sqrt{(X(\theta)_p^2 - X(\theta)_m^2)^2 + 2(X(\theta)_p^2 + X(\theta)_m^2)(p-m)^2 Z^2 + (p-m)^4 Z^4}}{2Z\text{Mod}(p-m)}$$

of two approximating contours, m and p and the final value for the polar curvature $\langle r_{p,m}(\theta) \rangle$ is computed as the average of radiuses $r_{p,m}(\theta)$ for as many pairs of contours p and m and Z is the differential path length between the contours p and m.

11. A method for determining the three dimensional external contour of the cornea, comprising:
    creating an OCT en-face two-dimensional composite image of the cornea in a common image plane with a multiple delay OCT instrument employing a reference beam and an object beam, wherein the optical path length difference between the object and reference beams has a plurality of values produced by a differential delay element, whereby said composite image lying in said common image plane created by said multiple delay OCT instrument contains a series of superimposed two dimensional image contours of the cornea taken from planes at different depths determined by the optical path length differences; and
    computing the three dimensional external contour of said curved object from said two dimensional contours in said common image plane and the known optical path length differences at the corresponding planes at different depths.

12. A method as claimed in claim 11, wherein the plurality of optical path length difference values is obtained by varying the optical path delay across the object beam or reference beam or source beam by introducing a delay element therein.

13. An apparatus for obtaining geometrical information about a curved object, comprising:
    an OCT imaging instrument for generating a composite en-face contour image of the curved object; and
    said OCT imaging instrument employing an output beam having parallel sub-beam portions associated with different path lengths so as to generate a set of two dimensional image contours at different image depths within the composite en-face image, said image contours having a known depth relationship determined by the differences in the optical path lengths; and
    a processor configured to compute the geometrical information from the image contours and the known depth relationship therebetween.

14. An apparatus as claimed in claim 13, further comprising a differential delay element creating said different path lengths, said delay element being in the form of a transparent block whose thickness varies in a stepwise manner across its width, the lateral size of the steps being less than the beam diameter divided by N+1, where N is the number of the plurality of optical path length differences.

15. An apparatus as claimed in claim 14, wherein the differential delay element is incorporated into the arm of the OCT interferometer leading to the object object.

16. An apparatus as claimed in claim 13, wherein further comprising a differential delay element creating said different path lengths in the form of multiple waveguides with different lengths.

17. An apparatus as claimed in claim 16, wherein said differential delay element comprises fiber patches of different length.

18. An apparatus as claimed in claim 13, further comprising a differential delay element creating said different path lengths, said differential delay element having portions intercepting the beam which vary according to the distribution of power within the transverse section of the beam.

19. An apparatus claimed in claim 13, further comprising an application module for approximating the contours in the en-face image with sharp contours.

20. An apparatus as claimed in claim 13, wherein said processor is configured to compute solutions for the curvature of the said object and for the axial distance away of said object from at least two distances between at least respectively three said contours and the lateral image size.

21. An apparatus as claimed in claim 13, further comprising an application module for computing an approximate axial distance by counting the number of contours in the composite en-face image and using the known optical path differences between the plurality of said beams.

22. A method of estimating the axial position of an object, comprising
    generating simultaneously a series of two dimensional image contours from planes at different image depths to create a two-dimensional composite en-face image in a common image plane using an OCT imaging instrument employing a reference beam and an object beam, wherein the optical path length difference between the object and reference beams has a plurality of values produced by a differential delay element, said planes at different depths having a known depth relationship determined by the differences in the optical path lengths at the different planes; and
    estimating the axial position of the object from the number of contours present in said composite image and the differential optical path differences between adjacent paths.

23. A method of obtaining geometrical information about an object, comprising:
    generating simultaneously a set of superimposed two dimensional image contours from planes at different depths to create a two-dimensional composite en-face image of the object in a common image plane using an OCT instrument employing a reference beam and an object beam, wherein the optical path length difference between the object and reference beams has a plurality of values produced by a differential delay element, said planes at different depths having a known depth relationship with each other; and
    computing the geometrical information about the object from said dimensional contours in said composite image and the known depth relationship between said planes at different depths.

24. A method as claimed in claim 23, wherein the geometrical information about the object is tilt or axial position.

25. A method as claimed in claim 24, wherein the shape of the said object is optimized for best accuracy of axial length measurement, or best sensitivity or depth range.

26. A method as claimed in claim 23, wherein the object is the cornea, and Purkinje reflections are added to the composite en-face image.

* * * * *